Sept. 17, 1935. D. BURPEE Plant Pat. 141
NASTURTIUM
Filed May 15, 1935
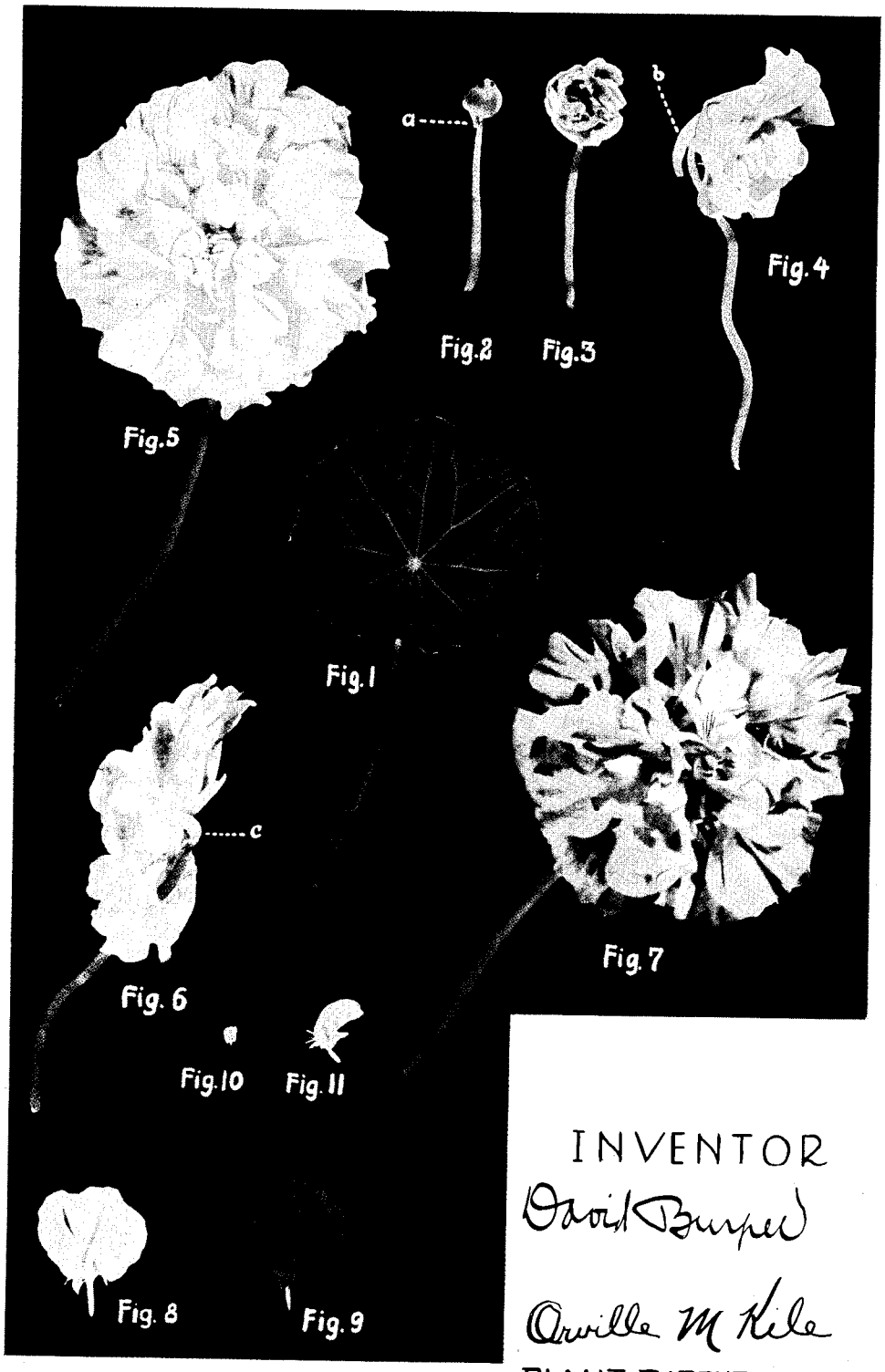
INVENTOR
David Burpee
Orville M Kile
PLANT PATENT AGENT Patented Sept. 17, 1935

UNITED STATES PATENT OFFICE

141

NASTURTIUM

David Burpee, Bucks County, Pa., assignor to W. Atlee Burpee Company, Philadelphia, Pa.

Application May 15, 1935, Serial No. 21,638

1 Claim. (Cl. 47—60)

My present invention relates to a new variety or genetic type of nasturtium (*Tropaeolum majus*) which possesses unusual vegetative vigor and produces an abundance of large, super-double, sterile flowers. Because of the extreme doubleness of its flowers this new variety of genetic type has been designated as *Tropaeolum majus* Burpeeii, a super-double-flowered type of *Tropaeolum majus*.

The origin and structural characteristics of this new and remarkable variety of nasturtium are herein described and illustrated. The accompanying illustrations are, in the originals, approximately natural size.

*Origin.*—This new super-double-flowered variety or type of nasturtium is a product of breeding experiments that have been carried on during the past several years on a large scale on the farms of the W. Atlee Burpee Company at Lompoc, California and at Doylestown, Pennsylvania. Experimental plants have also been grown by the W. Atlee Burpee Company at Miami, Florida; Villalba, Porto Rico; Buenos Aires, Argentina; Santiago, Chile; and Dundas, Australia. The growing of the experimental plants in such diversified localities doubtless exposed them to a great variety of environmental influences which may have been directly responsible for the mutational change represented by this new super-double-flowered type.

This super-double-flowered plant was discovered by me in one of the greenhouses on our Fordhook Farms at Doylestown, Pennsylvania. This plant was growing among several thousand experimental plants of Burpee's double hybrid nasturtiums. The plant was easily recognized by the flat button-like shape of its unfolding flower buds and the extreme doubleness of the open flowers.

Whether the gene for super-double flowers was induced by the exposure of the experimental plants to some environmental influence in one of the localities in which the plants were grown, or whether it was present in latent form in one of the parents used in the crosses, its expression was the result of experiments which were definitely planned for the creation of new varieties of *Tropaeolum majus*. This gene renders the flowers of the plant unable to produce seeds and increases the size and general magnificence of the flowers by greatly increasing the number of petals and by modifying the sex organs into petal-like structures.

Following discovery of this new nasturtium I removed it to another greenhouse and after proving its desirable characteristics, proceeded by well-known genetic methods to multiply both the quantity of stock and the number of colors.

*The plant-as-a-whole.*—The vegetative characteristics of the plant-as-a-whole resemble those of Burpee's double hybrid nasturtiums, its parents, except that the plant exhibits an increased vigor throughout its entire period or growth. The unusual vigor and the abundant production of large, super-double flowers appears to be associated with the inability of the plant to produce seeds.

*Stems.*—The stems are in general like the stems of other varieties or genetic types of the species but are distinctly thicker so that the whole plant has the appearance of being more massive than the other types.

*Leaves.*—The leaves differ in no important respects from the leaves of other varieties of the species, as may be seen from Fig. 1 of the accompanying plate.

*Buds.*—The extreme doubleness of the flowers of this new variety is apparent even in very young buds. The buds of the single as well as the double hybrid nasturtiums are heart-shaped with a long spur extending out from the large part of the heart. The buds of this new super-double variety are more or less spherical with a pointed tip when very young, as shown in Fig. 2. The spur is reduced in size and often appears as a mere rudiment. As the buds enlarge and open they assume a flat, button-like shape due to the large number of floral parts as illustrated in Fig. 3. The anterior (upper) petals usually enlarge more rapdily than the much-proliferated posterior (lower) petals so as to give to the flower a beautiful pansy-like shape, as may be seen in Fig. 4. When fully opened the doubleness of the flowers resembles that of a carnation as shown in Fig. 5 and Fig. 7.

*Flowers.*—The most important difference between the single- and double hybrid nasturtiums on the one hand and this new super-double nasturtium on the other, is concerned with the flowers.

The flowers of this new type are noticeably larger than the flowers of other types as may be seen from Figs. 5, 6 and 7. The average size of the flowers as determined by actual measurement is 3¼ inches in diameter. There is, of course, some variation in size, flowers sometimes reaching 3½ inches or more in diameter. It is this unusually large size and the extreme doubleness of the flowers which constitute the most important characteristics of this type.

The original of this new super-double nasturtium was golden yellow in color as shown in Fig. 5, but other colors are readily produced by means well known to horticulturists in a range extending from light primrose yellow, as shown in Fig. 8, through various shades of yellow, orange and scarlet, to deep maroon as shown in Fig. 9. Flowers of this super-double variety either have been or can readily be produced in all the colors that are inherent in the *Tropaeolum majus* species.

*Calyx.*—The calyx consists of five sepals, as in other types, but differs from that of others in having a more or less highly modified spur. The spur varies in size and is often reduced to a mere rudiment, as indicated by letters *a*, *b* and *c* in Figs. 2, 4 and 6. In some plants of this new variety the spur is inverted so that it extends with the petals toward the front of the flower.

*Corolla.*—The corolla is made up from 40 to 50 or even more petals (in addition to the smaller petal-like structures referred to below) which vary somewhat in size and shape as shown in Figs. 5, 6 and 7. The doubleness is expressed particularly in the clawed petals which form the lower part of the flower. The relatively small number of large upper petals together with the dense mass of proliferated lower petals create an effect distinctive from all other *Tropaeolum majus* types.

*Stamens.*—The stamens of the new variety are modified into petaloid structures (Fig. 11). The average number of petaloid stamens is 30. They materially contribute to the doubleness of the flower.

*Carpels.*—The carpels are greatly proliferated and are modified into petaloid or petal-like structures (Fig. 10) which are completely sterile. The extreme proliferation of the carpels, of which there are approximately 50, gives to the flower centers a characteristic fullness which accentuates and supplements the doubleness expressed in the petals and petaloid stamens.

*Receptacle.*—The receptacle is elongated to one-fourth of an inch to accommodate the unusually large number of floral parts. The total number of floral parts in the average super-double flower of this new variety is approximately 135 in contrast to 33 parts as the maximum number in the ordinary double flower and 21 parts in single flowers. The super-double flower thus has from six to seven times as many floral parts as a single flower while the ordinary double flower has only one-third more floral parts than a single flower.

*Reproduction.*—The flowers are incapable of producing seeds, but, like all other types of *Tropaeolum majus*, can readily be propagated asexually by cuttings.

Having thus disclosed my invention, I claim:

The variety or genetic type of nasturtium (*Tropaeolum majus*) herein described and illustrated, characterized particularly by its vigorous, stocky vegetative growth, and the unusually large size and complete doubleness of its flowers.

DAVID BURPEE.